US009972403B2

(12) United States Patent
Bowers et al.

(10) Patent No.: US 9,972,403 B2
(45) Date of Patent: May 15, 2018

(54) SELF-TESTING DATA STORAGE DEVICES AND METHODS

(71) Applicant: Elwha LLC, Bellevue, WA (US)

(72) Inventors: Jeffrey A. Bowers, Bellevue, WA (US); Peter L. Hagelstein, Carlisle, MA (US); Roderick A. Hyde, Redmond, WA (US); Muriel Y. Ishikawa, Livermore, CA (US); Jordin T. Kare, San Jose, CA (US); Lowell L. Wood, Jr., Bellevue, WA (US); Victoria Y. H. Wood, Livermore, CA (US)

(73) Assignee: Elwha LLC, Bellevue, WA (US)

( * ) Notice: Subject to any disclaimer, the term of this patent is extended or adjusted under 35 U.S.C. 154(b) by 0 days. days.

(21) Appl. No.: 14/683,998

(22) Filed: Apr. 10, 2015

(65) Prior Publication Data

US 2016/0133338 A1 May 12, 2016

Related U.S. Application Data

(63) Continuation of application No. 14/536,472, filed on Nov. 7, 2014.

(51) Int. Cl.
*G11C 29/38* (2006.01)
*G11C 29/42* (2006.01)
*G11C 29/44* (2006.01)
*G11C 29/56* (2006.01)

(52) U.S. Cl.
CPC ............. *G11C 29/38* (2013.01); *G11C 29/42* (2013.01); *G11C 29/44* (2013.01); *G11C 29/56* (2013.01)

(58) Field of Classification Search
CPC ........ G11C 29/38; G11C 29/44; G01K 1/024; G01N 27/121
USPC .......................................................... 714/763
See application file for complete search history.

(56) References Cited

U.S. PATENT DOCUMENTS

| 6,559,647 | B1 * | 5/2003 | Bidner | F02P 17/00 |
| | | | | 123/310 |
| 6,631,493 | B2 * | 10/2003 | Ottesen | G06F 3/0601 |
| | | | | 360/53 |
| 6,701,449 | B1 | 3/2004 | Davis et al. | |
| 6,850,379 | B2 | 2/2005 | Andoh et al. | |

(Continued)

*Primary Examiner* — James C Kerveros
(74) *Attorney, Agent, or Firm* — Foley & Lardner LLP (57) ABSTRACT

Systems and methods for self-testing archival memory devices are described. The memory device includes a data storage component capable of being coded with data. The memory device further includes a read-write mechanism configured to read, write, and delete data stored on the data storage component. The memory device includes a read-write controller configured to control the read-write mechanism based on input received through a device interface of the memory device, wherein the device interface of the memory device is configured to connect to an external computing device. The memory device further includes a diagnostic controller configured to perform a test on at least one of the data stored on the data storage component, the data storage component, and the read-write mechanism. The memory device includes a power source configured to provide operational power to the diagnostic controller when the memory device is not connected to an external power source.

30 Claims, 5 Drawing Sheets

(56) References Cited

U.S. PATENT DOCUMENTS

| | | | |
|---|---|---|---|
| 7,171,594 B2* | 1/2007 | Wyatt | G06F 11/0793 |
| | | | 714/704 |
| 7,600,051 B2 | 10/2009 | Clifton et al. | |
| 7,702,984 B1* | 4/2010 | Lee | G06F 12/1416 |
| | | | 365/185.33 |
| 8,327,054 B2* | 12/2012 | Ogino | G06F 11/106 |
| | | | 710/110 |
| 8,418,005 B2* | 4/2013 | Depew | G11C 29/50 |
| | | | 714/718 |
| 8,438,432 B2* | 5/2013 | Gupta | G11C 29/02 |
| | | | 714/718 |
| 8,443,263 B2 | 5/2013 | Selinger et al. | |
| 8,504,897 B2* | 8/2013 | Imagawa | G06F 11/1016 |
| | | | 714/768 |
| 8,689,082 B2 | 4/2014 | Oh et al. | |
| 9,070,473 B2* | 6/2015 | Bedeschi | G11C 16/3418 |
| 2005/0216800 A1* | 9/2005 | Bicknell | G06F 11/008 |
| | | | 714/718 |
| 2010/0174955 A1* | 7/2010 | Carnevale | G11O 5/04 |
| | | | 714/718 |
| 2015/0302924 A1* | 10/2015 | Bedeschi | G11C 16/3418 |
| | | | 714/764 |

* cited by examiner

SELF-TESTING DATA STORAGE DEVICES AND METHODS

CROSS-REFERENCE TO RELATED PATENT APPLICATIONS

This application is a continuation of U.S. patent application Ser. No. 14/536,472, filed Nov. 7, 2014, which is incorporated herein by reference in its entirety.

BACKGROUND

Entities, such as businesses and governments, often collect and/or generate large amounts of data. The data may relate to business transaction records, research information, media files, customer information, and the like. As data accumulates, the entities often store data in archival data storage devices, such as hard drives, CD-ROMs, DVD-ROMs, flash memory devices, and magnetic tape data storage devices (e.g., data cartridges, data cassettes, etc.). The archival data storage devices may be stored in remote facilities, such as warehouses or secure data centers. If certain archived data is later needed by the entity, the entity may locate the appropriate archival data device, connect the archival data device to a computing system (e.g., a desktop computer, a server, a laptop, etc.), and access the archived data via the computing system.

SUMMARY

One embodiment relates to a memory device. The memory device includes a data storage component capable of being coded with data. The memory device further includes a read-write mechanism configured to read, write, and delete data stored on the data storage component. The memory device includes a read-write controller configured to control the read-write mechanism based on input received through a device interface of the memory device, wherein the device interface of the memory device is configured to connect to an external computing device. The memory device further includes a diagnostic controller configured to perform a test on at least one of the data stored on the data storage component, the data storage component, and the read-write mechanism. The memory device includes a power source configured to provide operational power to the diagnostic controller when the memory device is not connected to an external power source.

Another embodiment relates to a memory device. The memory device includes a housing. The memory device further includes a data storage component coupled to the housing and configured to store data. The memory device includes a notification circuit coupled to the housing, wherein the notification circuit is configured to notify a user based on a determination that the memory device should be at least one of tested and replaced. The memory device further includes a power source coupled to the housing, wherein the power source provides operational power to the notification circuit.

An additional embodiment relates to a data storage and testing system. The system includes a data storage device. The data storage device includes a data storage component configured to store data, and a storage device interface configured to connect the data storage device to an external computing device. The system further includes a diagnostic attachment. The diagnostic attachment includes a diagnostic controller, an attachment interface configured to operatively connect the diagnostic attachment to the data storage device via the storage device interface, and a power source configured to provide operational power to the diagnostic controller. The diagnostic attachment is operatively coupled to the data storage device, the diagnostic controller is configured to perform a test on the data storage device.

Yet a further embodiment relates to a method of testing a data storage system that is in an archival state. The method includes powering a diagnostic controller of the data storage system with a power source of the storage system. The method further includes detecting, by the diagnostic controller, a trigger event. The method includes performing, by the diagnostic controller and based on detection of the trigger event, a test on the data storage system. The method further includes determining a result of the test.

An additional embodiment relates to a method of indicating a need for testing of a memory storage system in an archival state. The method includes powering a notification circuit of the memory storage system with a power source of the memory storage system. The method further includes detecting, by the notification circuit, a trigger event. The method includes providing, by the notification circuit and through a communication interface of the memory storage system, an alert based on detection of the trigger event.

The invention is capable of other embodiments and of being carried out in various ways. Alternative embodiments relate to other features and combinations of features as may be generally recited in the claims.

The foregoing is a summary and thus by necessity contains simplifications, generalizations, and omissions of detail. Consequently, those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Before turning to the figures, which illustrate the embodiments in detail, it should be understood that the application is not limited to the details or methodology set forth in the description or illustrated in the figures. It should also be understood that the terminology is for the purpose of description only and should not be regarded as limiting.

During storage, archival data devices may malfunction, deteriorate, become corrupted, or otherwise fail. Failure may be due to mechanical component failure and/or data corruption. For example, if left unused for extended periods of time, the motor that spins the platters of a hard drive, bearings within a hard drive, and/or the read-write head of the hard drive may malfunction or break. As an additional example, the data stored on the magnetic tape of a backup cartridge or the data stored on the platters of a hard drive may become corrupted. The malfunctions and failures may be caused by the normal degradation of components of the archival data devices over the course of time. The malfunctions and failures may be caused by external conditions in the storage center, such as exposure to humidity, fluctuating temperatures, exposure to magnetic fields, vibrations, etc. Since the archival data devices are not typically connected to computing systems during storage, the entities needing to access the archived data may not be aware of any malfunctions and failures until the archival data devices are accessed. Without a warning system in place, the archival data devices may fail or degrade to a point beyond repair and beyond data recovery.

Figure 1:
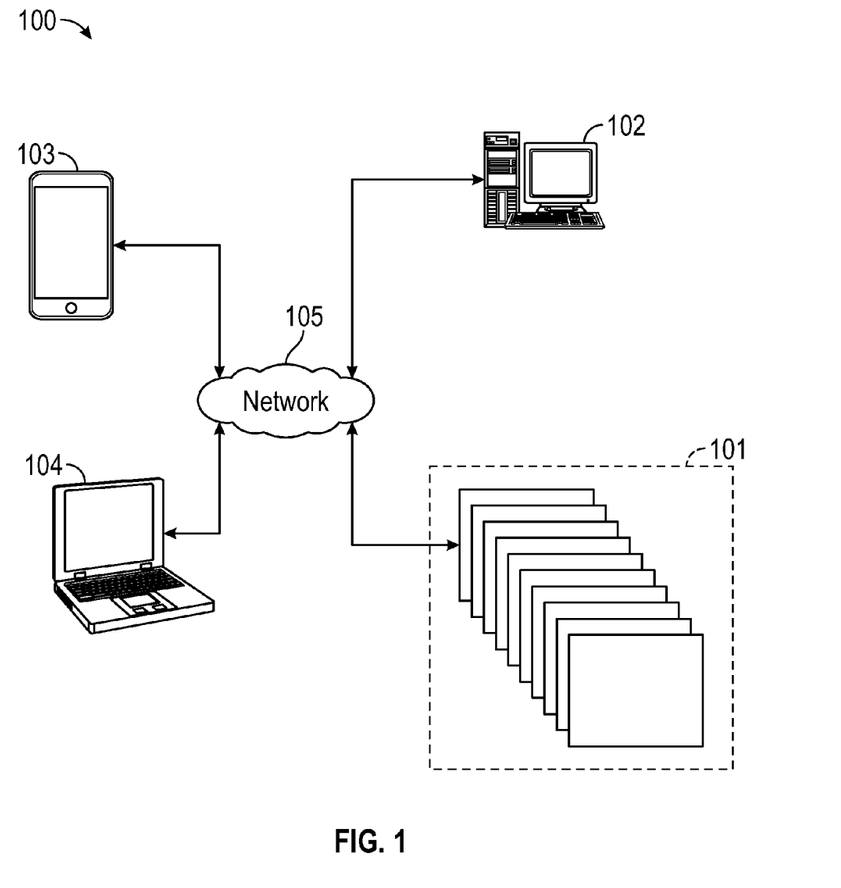
FIG. 1 is a schematic view of an archival data storage system according to an embodiment.

Referring to FIG. 1, archival data storage system 100 is shown according to an embodiment. System 100 includes a plurality of archived data devices 101. Archived data devices 101 may be hard drives, magnetic tape cartridges or cassettes, solid state memory devices, optical disk drives, or any combination thereof. Archived data devices 101 may be bare devices (e.g., a hard drive, a CD-ROM, a cartridge, etc.) or a device within an enclosure (e.g., a hard drive within a hard drive enclosure, a CD-ROM within a CD-Drive, a cartridge within a cartridge reader, etc.). The enclosure may have a power supply and/or a communication interface. Specific examples of archived data devices 101 are discussed below with respect to FIG. 2 and FIG. 3. Archived data devices 101 may be stored such that they are not connected to an external computing device, such as a desktop computer, a laptop computer, a server, or the like. For example, archived data devices 101 may be stored on shelves in a data warehouse or other offsite storage facility (i.e., offsite relative to a computer data center). Accordingly, archived data devices 101 may not be directly coupled to a computing device for normal read/write operation. For example, archived data devices 101 may have already been removed from computing devices previously used to write data to archived data devices 101 and placed on a shelf for long-term storage. Alternatively, data devices 101 may be installed within a computing device or other device (e.g., a recording device, etc.), which has itself been archived or otherwise shut down for an extended period of time. In another arrangement, data devices 101 may be installed in data systems, such as a disk array or a tape library, which may not activate or access the data device for extended periods of time.

As discussed in further detail below with respect to FIG. 2 and FIG. 3, archived data devices 101 are capable of performing various maintenance, diagnostic, and reporting functions without the need to be plugged into a computing device. Accordingly, archived data devices 101 may have built-in and independent power supplies, processing circuits, displays, lights, audio outputs, and/or communication interfaces. The communication interfaces may include remote warning systems (e.g., a contact closure, a radio frequency pulse emitter, an RFID tag that responds to a scanner, etc.). Archived data devices 101 may report statistics, statuses, error reports, and the like to computing devices, such as server 102, tablet computer 103, and computer 104. Archived data devices 101 may communicate directly with the computing devices or through network 105. Network 105 may be a local area network (e.g., a company specific intranet) or a wide area network (e.g., the Internet). Network 105 may communicate with devices using wireless networking components and protocols (e.g., WiFi, ZigBee, Bluetooth, 802.XX, GSM, CDMA, LTE, WiMax, etc.) and/or wired networking components and protocols (e.g., Ethernet).

Figure 2:
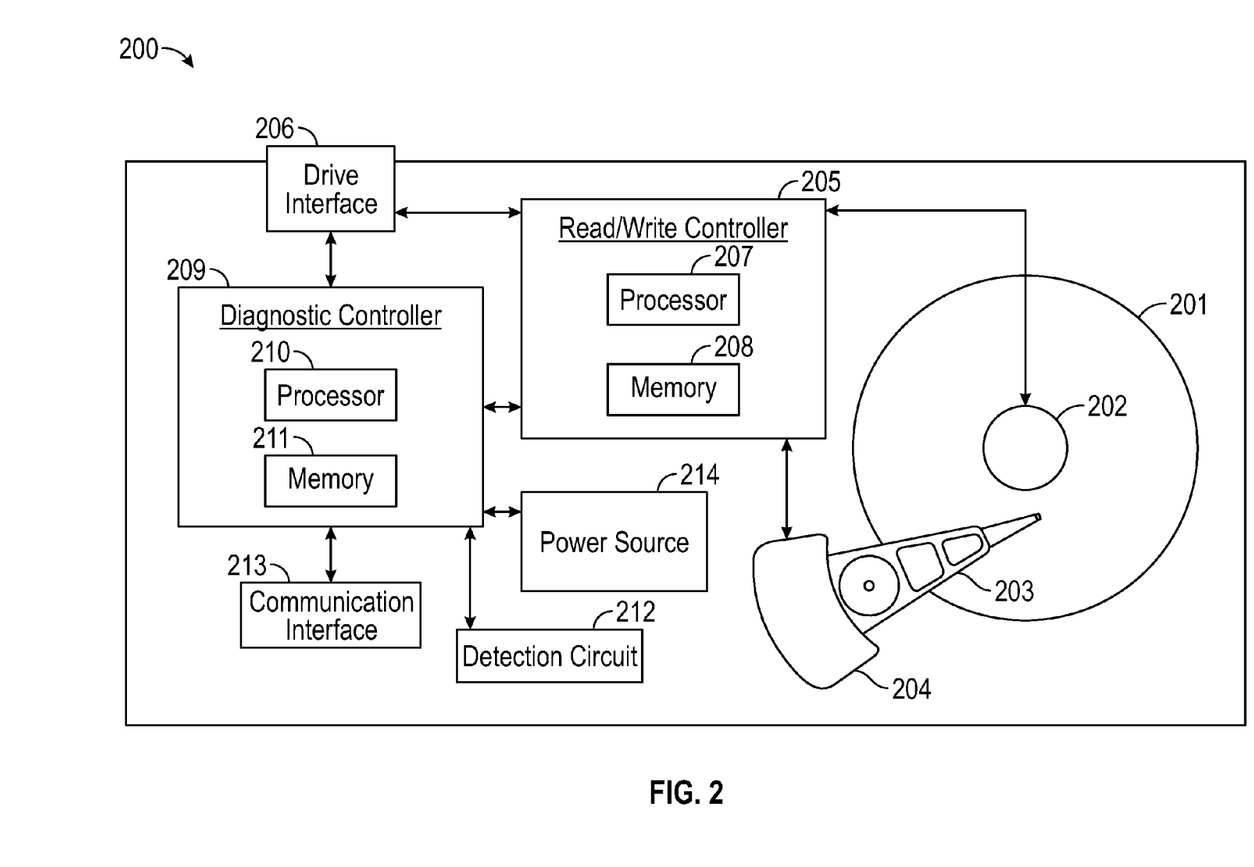
FIG. 2 is a block diagram of an embodiment of an archival data device.

Referring to FIG. 2, a block diagram of archival data device 200 is shown according to an embodiment. Device 200 includes a data storage component, shown as a plurality of platters 201. Platters 201 are arranged in a stacked arrangement. Platters 201 are coated with a magnetic material capable of being written with data. Platters 201 are rotated during reading and writing operations by spindle motor 202. Data may be written to, read from, or deleted from platters 201 by a read/write mechanism, shown as head assembly 203. Head assembly 203 is positioned along platters 201 by head actuator 204. Head actuator 204 rotates head assembly 203 such that the head assembly 203 can read, write, or delete data at various positions along platters 201 while platters 201 are spinning. Read-write controller 205 controls spindle motor 202, head assembly 203, and head actuator 204 to perform data reading, data writing, and data deletion operations based on input received from a computing system (e.g., a laptop computer, a server, etc.) connected to device 200 through drive interface 206. In some embodiments, device 200 is not a traditional stand-alone computing device such as a laptop or desktop computer. As such, device 200 may not include features such as a display screen, a keyboard, a mouse, etc. Although device 200 is shown as a hard drive, the same and/or similar principles may be applied to magnetic tape cartridges or cassettes, solid state memory devices, optical disk drives, or any combination thereof.

Read-write controller 205 includes processor 207 and memory 208. Memory 208 stores programming modules that, when executed by processor 207, control the operation of device 200 based on input received via drive interface 206. Memory 208 may include read-only memory ("ROM") and/or random-access memory ("RAM"). RAM may also be used as a cache device for data stored on device 200 or for data to be written to device 200.

Interface 206 includes an electronic data bus, which enables a connected computing device to instruct read-write controller 205 to perform data operations. The electronic data bus may be a standard data device bus type, such as IDE, SATA, E-SATA, SCSI, SAS, IEEE 1394, USB, Thunderbolt, Fibre Channel, ESCON, fiber optic etc. Interface 206 may include a plurality of types of electronic data buses for communicating with external computing devices over a plurality of different protocols. Interface 206 may also provide operational power to device 200 from an external power supply (e.g., the power supply of the connected computing system).

Device 200 includes diagnostic controller 209. Diagnostic controller 209 may be configured to perform various diagnostic tests and maintenance tasks on device 200 when device 200 is not connected to a computing device via interface 206. For example, diagnostic controller 209 may be configured to perform a diagnostic test on device 200 when device 200 is stored (e.g., on a shelf of a data storage center). In some arrangements, diagnostic controller 209 may perform the various diagnostic tests and maintenance tasks on device when device is connected to a computing device via interface 206. In such an arrangement, diagnostic controller 209 may receive commands from the connected computing device. The diagnostic and maintenance tasks may include both functional tests (e.g., spinning up of motor 202, movement of head assembly, etc.), data integrity tests (e.g., data corruption tests, random data read/write sequences, platter status tests, data integrity tests, etc.), and/or environmental tests (e.g., ambient temperature readings, ambient humidity readings, vibration tests, etc.). A data integrity test may be a limited data test (e.g., a test of a random file, a random block of data, a previously specified file, etc.) or a full data test on all data within device 200. Diagnostic controller 209 may determine whether to perform a limited data test or a full data test based on an amount of power available, an indicated importance of the files, the time since the last test, results of previous data tests, and/or user settings.

Diagnostic controller 209 includes processor 210 and memory 211. Similar to memory 208 of read-write controller 207, memory 211 stores programming modules that, when executed by processor 210, perform various testing and maintenance functions on device 200. Memory 211 may include ROM and/or RAM. Memory 211 may be programmed with programming modules by a computing device connected to device 200 through interface 206. In alternative arrangements, memory 211 may be preprogrammed by a manufacturer of device 200.

In some embodiments, device 200 includes detection circuit 212. Detection circuit 212 may be configured to detect a characteristic and to provide a feedback signal indicative of the detected characteristic to diagnostic controller 209. The feedback signal may be used by diagnostic controller 209 in performing and/or triggering various diagnostic tests and/or maintenance functions on device 200. Detection circuit 212 may include a sensor configured to provide a feedback signal to diagnostic controller 209 indicative of a sensed characteristic. The sensor may be a temperature sensor configured to sense the temperature within device 200 or an ambient temperature external to device 200. The sensor may be a humidity sensor configured to sense a humidity of the air within device 200 or external to device 200. The sensor may be a vibration sensor or a motion sensor configured to sense vibrations and movements experienced by device 200. The sensor may be a magnetic field sensor configured to sense magnetic fields experienced by device 200. In some embodiments, detection circuit 212 includes a timer. The timer may be configured to provide diagnostic controller 209 an indication of the present time, an indication of the present date, and/or a status of a running timer (e.g., the amount of time remaining on a countdown timer).

According to one embodiment, device 200 further includes communication interface 213. Communication interface 213 may be electronically coupled to diagnostic controller 209. Communication interface 213 may include a wireless transmitter (e.g., WiFi, ZigBee, Bluetooth, 802.XX, GSM, CDMA, LTE, WiMax, infrared, etc.) or wired transmitter. The transmitter may be a transceiver. In such an arrangement, diagnostic controller 219 can send data relating to performed diagnostic tests and maintenance tasks to an external computing device (e.g., server 102, tablet computer 103, and computer 104) through communication interface 213. Diagnostic controller 209 may communicate directly with the external computing device or indirectly through a network (e.g., network 105). The data communicated through interface 213 may relate to a message relating to a status of device 200. The message may include a warning that device 200 has failed or may fail. The warning may include specific information such as a type of failure or type of expected failure (e.g., data corruption, mechanical component failure, head assembly crash, etc.). The warning may include information relating to conditions of device 200 (e.g., a temperature of device 200) or conditions of the storage environment (e.g., a temperature of the storage environment, a humidity of the storage environment, detected vibrations, magnetic field intensity, etc.). The message may include an indication that device 200 has passed a diagnostic test or an indication that a maintenance task was performed.

In some arrangements, communication interface 213 may emit communication signals perceivable by people. For example, communication interface 213 may include a light source. The light source may be a multi-colored LED. Diagnostic controller 209 may emit a status light to indicate a status of device 200 or the results of a diagnostic test performed on device 200. Different messages may be conveyed through the use of different colors and/or pulsed light patterns. For example, the light source may emit a green light if the device has passed all of the diagnostic tests and a red light if a diagnostic test has failed. The red light serves as an indication to a person (e.g., an employee in the storage warehouse) that device 200 should have its data backed up and/or connected to a computing device to perform additional tests. As another example, communication interface 213 may include a speaker. Diagnostic controller 209 may emit an audible alert to indicate a status of device 200 or the results of a diagnostic test performed on device 200. For example, the speaker may emit a warning beep or tone if device 200 has failed a diagnostic test. The warning beep or tone serves as an indication to a person (e.g., an employee in the storage warehouse) that device 200 should have its data backed up and/or connected to a computing device to perform additional tests. In other arrangements, communication interface 213 communicates with electronic devices. For example, the communication interface 213 may include a contact closure, a radiofrequency pulse emitter, an RFID tag capable of being read by an external computing device, etc.

In some arrangements diagnostic controller 209 is configured to perform a data protection action. The data protection action may be performed after device 200 fails a given test. The data protection function is intended to preserve data in case of device 200 failure or to repair data that has become corrupted on device 200. Diagnostic controller 209 may transmit data at risk of being lost due to device 200 failure or a potential failure of device 200 to an external computing system through communication interface 213 (e.g., to server 102). Alternatively or in addition to transmitting data to the external computing device, diagnostic controller 209 may attempt to repair corrupted data files stored on device 200. Diagnostic controller 209 may repair the data files through the use of error correcting codes.

Referring further to FIG. 2, device 200 includes power source 214. Power source 214 may provide sufficient operational power to the components of device 200 when device 200 is not connected to an external power source (i.e., a power supply of a computer device connected to device 200 via interface 206). Power source 214 may be a battery. Power source 214 may be a high capacity battery, such as a lithium polymer battery. Power source 214 may be a rechargeable battery. A status of the rechargeable battery may be presented to a user through communication interface 213 (e.g., an LED can indicate to the user when the rechargeable battery needs to be charged by pulsing a red light). Power source 214 may be a hyper capacitor or a super capacitor. Power source 214 may be configured to harvest energy from the ambient environment (e.g., via a solar panel such as a photovoltaic panel). Power source 214 may include a wireless energy receiver, such as an inductive power supply. In some storage arrangements, device 200 may be plugged into an external power source (e.g., grid power)

such that device 200 may receive operational power when device 200 is not connected to a computing device via interface 206.

As discussed above, device 200 includes diagnostic controller 209, which is separate from read-write controller 205. In an alternative arrangement, read-write controller 205 may be programmed to perform the above-described functions of diagnostic controller 209 in addition to its standard data operation functions. In such an arrangement, an additional controller (e.g., diagnostic controller 209) is not needed to perform diagnostic tests and maintenance tasks on device 200 when device 200 is not connected to a computing device via interface 206.

Figure 3:
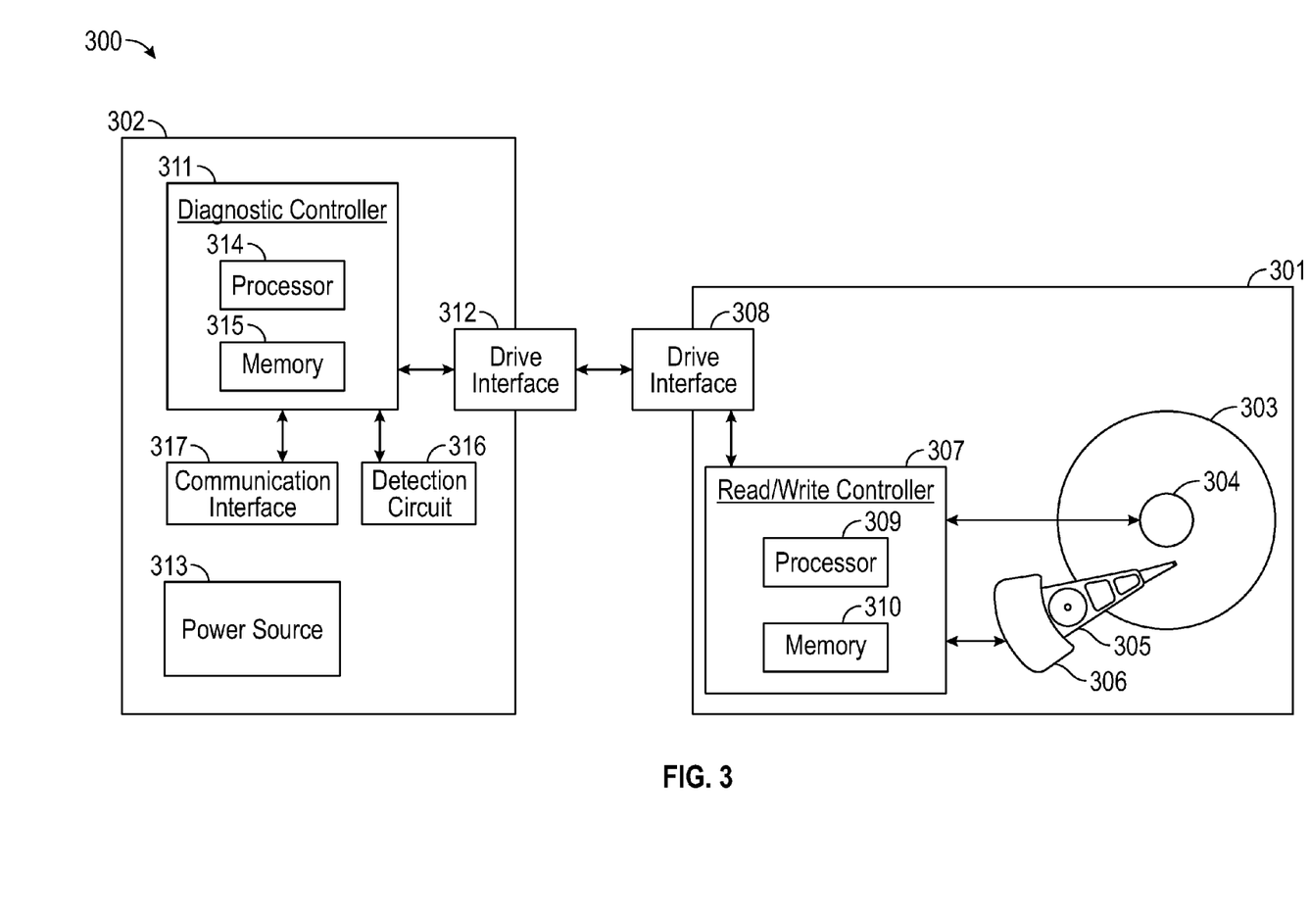
FIG. 3 is a block diagram of an embodiment of an archival data device peripheral.

Referring to FIG. 3, a block diagram of archival data storage system 300 is shown according to an embodiment. System 300 includes data storage device 301 and diagnostic attachment 302. Together, device 301 and attachment 302 include similar components to device 200, but provided by two physically separate devices. System 300 functions in a similar manner to device 200 as described above with respect to FIG. 2.

Device 301 includes a plurality of platters 303. Platters 303 are arranged in a stacked arrangement. Platters 303 are coated with a magnetic material capable of being written with data. Platters 303 are rotated during reading and writing operations by spindle motor 304. Data may be written to, read from, or deleted from platters 303 by head assembly 305. Head assembly 305 is positioned along platters 303 by head actuator 306. Head actuator 306 rotates head assembly 305 such that the head assembly 305 can read, write, or delete data at various positions along platters 303 while platters 303 are spinning. Read-write controller 307 controls spindle motor 304, head assembly 305, and head actuator 306 to perform data reading, data writing, and data deletion operations based on input received from a computing system (e.g., a laptop computer, a server, etc.) connected to device 301 through drive interface 308. Read-write controller 307 includes processor 309 and memory 310. Memory 310 stores programming modules that, when executed by processor 309, control the operation of device 301 based on input received via drive interface 308. Memory 310 may include read-only memory ("ROM") and/or random-access memory ("RAM"). RAM may also be used as a cache device for data stored on device 301 or for data to be written to device 301.

Device 301 is shown as a hard drive, but the same and/or similar principles may be applied to magnetic tape cartridges or cassettes, solid state memory devices, optical disk drives, or any combination thereof. Device 301 may not be a stand-alone computing device (e.g., a laptop or a desktop computer), and hence may not include typical stand-alone computing devices and peripherals, such as a user input (e.g., a keyboard, a mouse) or a display. Device 301 may be connected to an external computing device, such as a laptop, a desktop computer, an external drive enclosure, etc. through interface 308.

Interface 308 includes an electronic data bus, which allows a connected computing device to instruct read-write controller 307 to perform data operations. The electronic data bus may be a standard data device bus type, such as IDE, SATA, E-SATA, SCSI, SAS, IEEE 1394, USB, etc. Interface 308 may include a plurality of types of electronic data buses for communicating with external computing devices over a plurality of different protocols. Interface 308 may also provide operational power to device 301 from an external power supply (e.g., the power supply of the connected computing system).

Unlike device 200, device 301 does not include a separate diagnostic controller. Rather, device 301 connects to attachment 302, which includes an external diagnostic controller 311. Attachment 302 connects to device 301 through interface 312. Interface 312 is configured to mate with interface 308 of device 301. Accordingly, interface 312 includes an electronic data bus, which allows attachment 302 to communicate with read-write controller 307 to perform data testing and diagnostic operations. The electronic data bus may be a standard data device bus, such as IDE, SATA, E-SATA, SCSI, SAS, IEEE 1394, USB, etc. Interface 312 may include a plurality of types of electronic data buses for communicating with external computing devices over a plurality of different protocols. Interface 312 may also provide operational power to device 301 from an internal power supply (e.g., power source 313).

Diagnostic controller 311 may be configured to perform various diagnostic tests and maintenance tasks on device 301 when attachment is coupled to device 301 via interfaces 308 and 312. Diagnostic controller 311 may perform the same tests on device 301 as diagnostic controller diagnostic controller 209 may perform on device 200 as discussed above with respect to FIG. 2. Diagnostic controller 311 includes processor 314 and memory 315. Memory 315 stores programming modules that, when executed by processor 314, perform various testing and maintenance functions on device 301. Memory 315 may ROM and/or RAM. Memory 315 may be programmed with programming modules by a computing device connected to attachment 302 through interface 312. In alternative arrangements, memory 315 may be preprogrammed by a manufacturer of attachment 302.

Attachment 302 includes detection circuit 316. Detection circuit 316 is configured to detect a characteristic and is configured to provide a feedback signal to diagnostic controller 311 indicative of the characteristic. Detection circuit 316 may include any of the above-described sensors of detection circuit 212.

Attachment 302 includes communication interface 317. Communication interface 317 may have the same configuration as communication interface 213 of device 200. Accordingly, communication interface 317 may be configured to perform the same functions as communication interface 213 as described above with respect to FIG. 2.

In some diagnostic controller 311 of attachment 302 may be configured to perform a data protection action. The data protection action may be performed after device 301 fails a given test or after an indication that device may be about to fail. The data protection action performed by diagnostic controller 311 may be any of the same data protection actions performed by diagnostic controller 209 as discussed above with respect to FIG. 2.

Attachment 302 includes power source 313. Power source 313 provides operational power to the above-described components of attachment 302. Additionally, power source 313 may provide operational power to device 301 when device 301 is connected to attachment 302 via interfaces 308 and 312. Power source 313 may include any of the above-described features of power source 214 as described with respect to FIG. 2.

Figure 4:
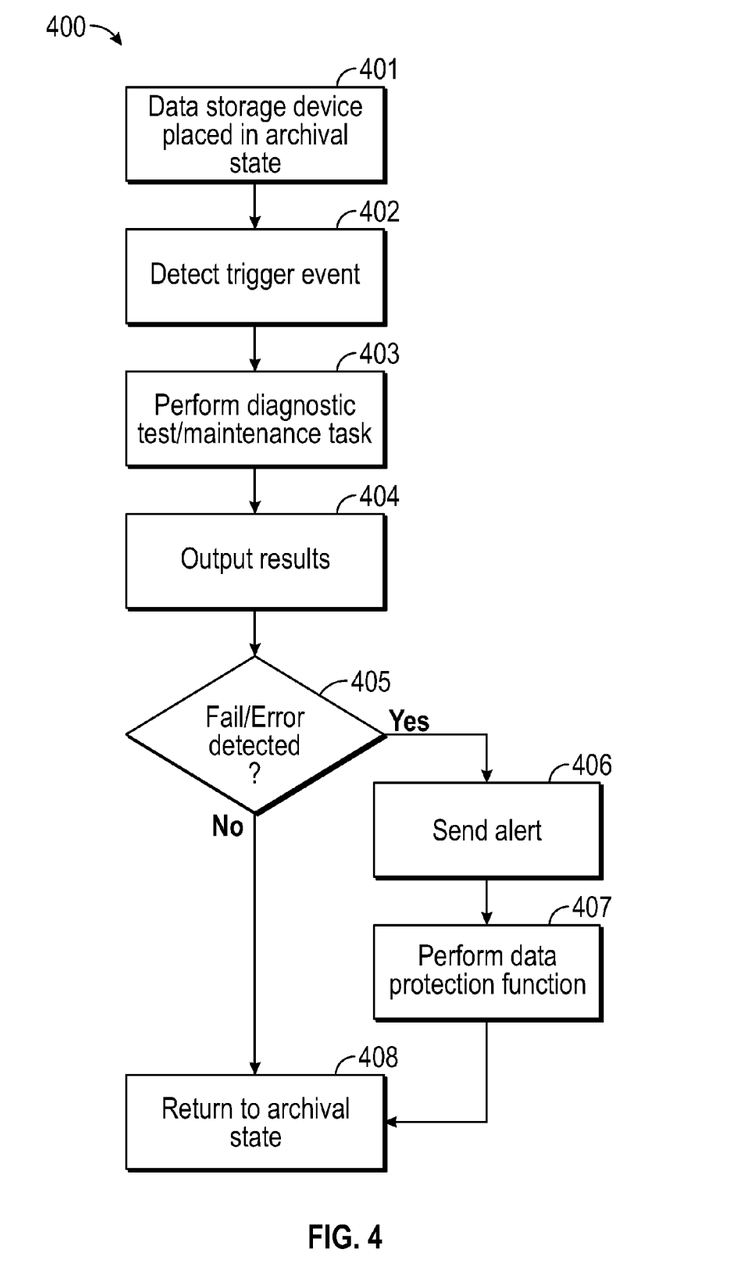
FIG. 4 is a flow chart of a method of monitoring an archival data device.

Referring to FIG. 4, a flow chart of a method 400 of performing a diagnostic test or maintenance task on an archival storage device (e.g., devices 101, device 200, system 300, etc.) in an archival storage system is shown.

The archival data storage device is placed in an archival state (401). The archival data storage device may be a hard drive, a flash memory device, a magnetic tape data storage device (e.g., data cartridges, data cassettes, etc.), or other storage devices. In some embodiments, the archival data storage device is placed in the archival state by disconnecting it from the computing device that was utilizing the archival data storage device as a data storage device (e.g., by disconnecting the archival data storage device from a server). The archival data storage device may include a diagnostic controller (e.g., diagnostic controller 209) and an independent power source (e.g., power source 214). Placing the archival data storage device in the archival state may involve activating a switch or a jumper that activates the diagnostic controller. In an alternative arrangement, the archival data storage device is automatically placed in an archival state when it is connected with an independent diagnostic attachment having a diagnostic controller and a power source (e.g., attachment 302 of system 300). In another alternative arrangement, the archival data storage device is automatically placed in an archival state when it is disconnected from an external computing device. For example, when archival data device is removed from a server an internal diagnostic controller determines that the archival data device has been disconnected and automatically places the device in an archival state.

When placed in the archival state, the diagnostic controller is configured to activate and test the archival storage device. The activation and testing of the archival storage device is done to perform various diagnostic tests and maintenance tasks on the archival storage device when the archival storage device is in the archival state. The diagnostic and maintenance tasks may include any of mechanical maintenance tasks (e.g., spooling up of motor 202, movement of head assembly, etc.), data integrity tests (e.g., data corruption tests, random data read/write sequences, platter status tests, etc.), and/or environmental tests (e.g., ambient temperature readings, ambient humidity readings, vibration tests, etc.). A data integrity test may be a limited data test (e.g., a test of a random file, a random block of data, a previously specified file, etc.) or a full data test on all data within data device. The diagnostic controller of the data device may decide whether to perform a limited data test or a full data test based on an amount of power available, an indicated importance of the files, the time since the last check, the results of previous data tests, and/or user settings.

The activation and testing occurs when a trigger event occurs (402). The diagnostic controller may detect the trigger event. The trigger event may be detected based on a feedback signal received from a detection circuit within the archival storage device or within the independent diagnostic attachment. The detection circuit is configured to detect a characteristic and is configured to provide a feedback signal to diagnostic controller indicative of the characteristic. The detection circuit may include a sensor configured to provide a feedback signal to the diagnostic controller indicative of a sensed characteristic. The sensor may be a temperature sensor configured to sense the temperature of archival data storage device and/or the temperature of the ambient storage environment. The sensor may be a humidity sensor configured to sense a humidity of the air within or external to the archival data storage device. The sensor may be a vibration sensor or a motion sensor configured to sense vibrations and movements experienced by the archival data storage device. The sensor may be a magnetic field sensor configured to sense magnetic fields experienced by the archival data storage device. The trigger event may relate to a threshold level sensed by the detection circuit. For example, the trigger event may occur when the temperature exceeds a threshold temperature, when the humidity exceeds a threshold humidity, when the movement of the archival data storage device exceeds a threshold movement value (e.g., a threshold speed, a threshold acceleration, etc.), when the magnetic field experienced by the archival data storage device exceeds a threshold magnitude, or a combination thereof. Alternatively, the trigger event may relate to a time integral of a function of the detected characteristic exceeding a predetermined value. For example, if the storage device is maintained in an environment having a variable temperature or humidity environment, the trigger event may relate to a time integral of the amount of time the storage device spends in the environment when the temperature is above a set temperature or the humidity is above a set humidity. In other arrangements, the activation may be periodic (i.e., according to a set fixed interval) or according to a random pattern.

The detection circuit may include a timer. The timer may be configured to provide the diagnostic controller an indication of the present time, an indication of the present date, and/or an indication of a running timer. The trigger event may be a specific time, a specific date, or an amount of time since the last diagnostic test or maintenance function was performed (e.g., the expiration of a running countdown timer). A specific time period (e.g., the length of a running countdown timer) may be shortened or lengthened based on feedback signals from any of the above-described sensors. For example, if the periodic activation for testing is to occur every set time period (e.g., every week, every month, etc.), the time period may be reduced if the archival storage device experiences unanticipated high temperatures, high humidity, strong magnetic fields, and/or large quantities of movements or vibrations. Likewise, the time period may be lengthened if the archival storage device experiences optimal temperatures, humidity, magnetic fields, and/or movements and vibrations. The degree to which the time period is reduced or lengthened may depend on magnitudes of the sensed properties. The trigger event may relate to a recurring timed event (e.g., every week, every month, every 100 hours, etc.). The recurring time period may be reset by an external event such as a manual reset by the user (e.g., by pressing a manual reset button, by receiving an instruction from the user through a communication interface of the archival storage device, etc.), a manual powering up of the archival storage device, connection with an external computing device, or the like.

In an alternative arrangement, the trigger event may be an on demand activation and testing request based on a user input. The user input may be provided through a switch or a button on the archival data device or an independent diagnostic attachment. Alternatively, the user input may be provided remotely through an electronic signal (e.g., sent from a computing device over a network and received by the diagnostic controller through a communication interface of the archival data device or the independent diagnostic attachment).

After the trigger event is detected, the diagnostic controller performs a diagnostic test and/or a maintenance task on the archival storage device (403). The diagnostic and maintenance tasks may include any of mechanical maintenance tasks or tests (e.g., spooling up of motor 202, movement of head assembly, etc.), data integrity tests (e.g., data corruption tests, random data read/write sequences, platter status tests, etc.), and/or environmental tests (e.g., ambient temperature readings, ambient humidity readings, vibration tests, etc.). In some testing arrangements, the test itself may utilize the detection circuit in analyzing the archival storage device. For example, the detection circuit may include a current meter configured to measure the current draw of an electric motor of the archival storage device. During the test, the electric motor may be activated (e.g., motor 202 may be activated to rotate platters 201). The current meter may measure an abnormal current requirement from the motor, which may indicate that the motor or a component within the motor (e.g., bearings, brushes, etc.) may be likely to fail. As an additional example, the detection circuit may include a temperature sensor. The diagnostic controller may determine that operation of the motor is creating an abnormal amount of heat, which may indicate that the motor or a component within the motor may be likely to fail. Still further, the detection circuit may include a motion and/or vibration sensor. The diagnostic controller may determine that operation of the motor is creating an abnormal amount of vibrations, which may indicate that the motor or a component within the motor may be likely to fail. In some arrangements, the diagnostic controller may perform a single test (e.g., operation up of a motor). In other arrangements, the diagnostic controller may perform a series of tests on the archival storage device.

In some arrangements, after the diagnostic test has concluded, the results of the diagnostic test and/or the maintenance task are output, for example, to a memory of the diagnostic controller or to an external computing device (404). The diagnostic controller may include memory. The memory is configured to store a log of test results. The log may include a time of the test, a date of the test, a type of test, a test result (e.g., pass or fail), and an error condition or code if an error was detected. An external computing device may access the memory of the diagnostic controller through a communication interface. The diagnostic controller may be configured to automatically upload or transmit the log and/or any individual test results to an external computing device (e.g., server 102). The upload may consist of a data file including an identification of the archival memory device.

After the test has been completed, the system determines whether a the archival memory device failed the test or whether an error was detected during the diagnostic test and/or maintenance task (405). If an error or a failure was detected, an alert is initiated (406). The diagnostic controller may initiate an alert through a communication interface. The communication interface may include a light (e.g., an LED) visible by a user. The light may be activated to indicate that an error was detected or a failure occurred. The light may be activated in different colors to indicate different types of errors or failures. The different colors may correspond to a severity of the detected error or failure. The light may be pulsed according to a pattern to indicate the type of detected error or failure. The communication interface may include a speaker. The speaker may emit a tone or a spoken message to indicate that an error or failure was detected. The tone may be pulsed according to a pattern to indicate the type of detected error or failure. The tone may be emitted at different frequencies to indicate the type of detected error or failure. The spoken message may generically indicate that an error or failure occurred. Alternatively, the spoken message may specifically indicate the type of error or failure that occurred.

The alert may be initiated via an electronic signal sent from the communication interface to an external device (e.g., server 102, tablet 103, computer 104, a cell phone, a PDA, etc.). The alert may be sent as a message (e.g., e-mail, SMS, MMS, voicemail, etc.). The message may include a time of the test, a type of the test, the type of error or failure that occurred, and/or recommended action to be taken (e.g., back up the archival storage device, connect the archival storage device to an external computing device for further testing, repair the archival storage device, etc.).

Additionally, if an error condition or fail condition was detected, the system may perform a data protection action (407). The data protection action may be performed after the device fails a given test. The data protection function is intended to preserve data in case of a device failure or to repair data that has become corrupted on the device. The diagnostic controller may transmit data at risk of being lost due to the device's failure or a potential failure of the device to an external computing system through a communication interface (e.g., to a remote server). Alternatively or in addition to transmitting data to the external computing device, the diagnostic controller may attempt to repair corrupted data files stored on the device. The diagnostic controller may repair the data files through the use of error codes.

If no error condition or fail condition was detected, or after taking appropriate action in response to any failures or errors, the archival storage device is returned to the archival state (408). In some arrangements, a message may be sent via the communication interface to the external computing device to indicate that the device is in a normal state if no error condition or fail condition was detected (e.g., an all-clear message). The process may repeat with every detected trigger event.

Figure 5:
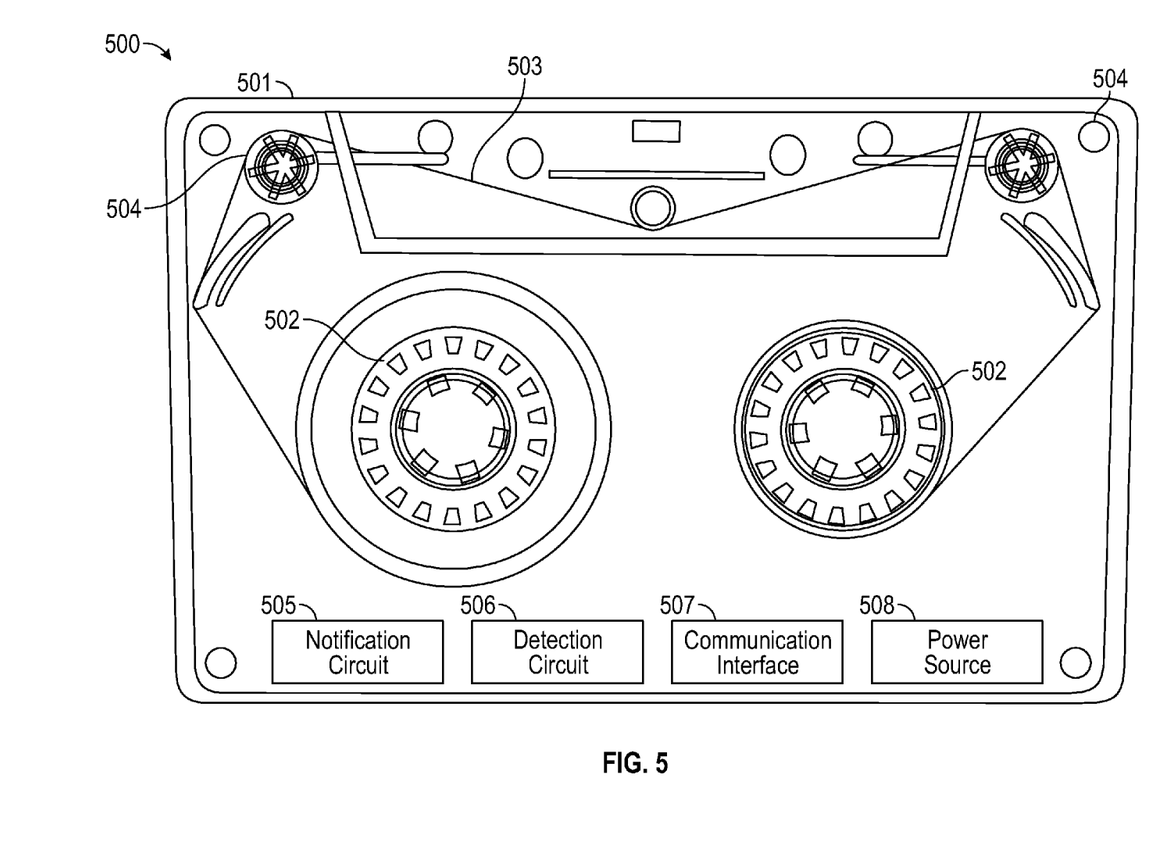
FIG. 5 is a block diagram of another embodiment of an archival data device.

FIG. 5 is a block diagram of an embodiment of an archival data device 500. Device 500 is a magnetic tape backup cartridge. Device 500 includes housing 501. Device 500 includes two reels 502 and magnetic tape 503. In one embodiment, magnetic tape 503 includes a thin, plastic substrate having a magnetizable coating configured to store data. Magnetic tape 503 may be written to by an external drive configured to receive device 500. Device 500 includes tension pins 504. Although shown as including two tension pins 504, device 500 may include any number of tension pins 504.

Device 500 is configured to notify a user when device 500 should be tested. Accordingly, device 500 includes notification circuit 505. Notification circuit 505 is similar to diagnostic controller 209 of device 200. Accordingly, notification circuit 505 may include a processor and memory. The memory may store programming modules that, when executed by the processor, control the operation of notification circuit 505. The memory may include ROM and/or RAM. However, unlike device 200, device 500 may not include any motors or actuators. Alternatively, device 500 includes motors and actuators, but device 500 is not configured to activate the motors and actuators when in an archived state (e.g., no operational power is provided to the motors and actuators when in the archived state). Reels 502 are spun by motors located within the drive in which device 500 is received. Accordingly, notification circuit 505 may not be programmed to perform actual diagnostic tests or maintenance tasks on device 500. Rather, notification circuit 505 may be programmed to alert a user that it may be necessary to insert device 500 into a receiving drive capable of performing test and/or maintenance tasks. Notification circuit 505 may store a log of sent messages and alerts in the memory.

Device 500 includes detection circuit 506. Detection circuit 506 is configured to detect a characteristic and is configured to provide a feedback signal to notification circuit 505 indicative of the characteristic. Detection circuit 505 operates in a similar manner to detection circuit 212 and to detection circuit 316. Accordingly, detection circuit 505 may include any of the above-described sensors of detection circuit 212 and detection circuit 316.

The alert sent by notification circuit 505 may be initiated based on any of the sensed characteristics. An alert may be initiated by notification circuit 505 if a sensed temperature, a sensed humidity, and/or a sensed magnetic field magnitude exceeds threshold values. Alternatively, the alert may relate to a time integral of a function of the detected characteristic exceeding a predetermined value. For example, if the storage device is maintained in an environment having a variable temperature or humidity environment, the alert may relate to a time integral of the amount of time the storage device spends in the environment when the temperature is above a set temperature or the humidity is above a set humidity. An alert may be initiated by notification circuit 505 if device experiences an unexpected or rapid movement (e.g., if device 505 falls off of a shelf). An alert may be initiated after an expiration of time. The expiration of time may be a recurring time period (e.g., an alert initiated every week or month) or based on a time device 500 was last tested or used. The recurring time period may be shortened or lengthened based on feedback from detection circuit 505 (e.g., shortened or lengthened based on the same characteristics as described above with respect to the detection circuit of method 400). The alert may be initiated based on a calendar (e.g., every Monday, once a month, once a year, etc.). The alert or message may relate to non-alarm signals that are periodically sent to verify that notification circuit 505 is functioning.

Device 500 includes communication interface 507. Communication interface 507 is operatively coupled to notification circuit 505. Communication interface 507 may have the same configuration as communication interface 317 of attachment 302 and of communication interface 213 of device 200. Accordingly, communication interface 507 may be configured to deliver messages and alerts in a similar manner to communication interface 213 as described above with respect to FIG. 2 and to communication interface 317 as described above with respect to FIG. 3. The message or alert may include a warning that device 500 needs to be tested in a drive. The message may include information relating to conditions of device 500 (e.g., a temperature of device 500) or conditions of the storage environment (e.g., a humidity of the air in the storage environment, detected vibrations, etc.). Alternatively, the message or alert may indicate that device does not need to be tested (e.g., an all-clear message). The messages may be electronically transmitted messages (e.g., an e-mail, a text message, etc.), or indications that are perceivable by a person walking by the device (e.g., the lighting of a light, a message displayed on a low power e-ink display system, etc.).

In one embodiment, device 500 includes power source 508. Power source 508 provides operational power to notification circuit 505, detection circuit 506, and communication interface 507. Power source 508 may include any of the above-described features of power source 214 as described with respect to FIG. 2 and/or of power source 313 as described with respect to FIG. 3. Power source 508 may be a high capacity battery, such as a lithium polymer battery. Power source 508 may be a rechargeable battery. A status of the rechargeable battery may be presented to a user through communication interface 507 (e.g., an LED can indicate to the user when the rechargeable battery needs to be charged by pulsing a red light).

Although device 500 is shown as a magnetic tape cassette or cartridge, similar concepts may be applied to other memory devices. For example, a hard drive, a flash memory device, a CD-ROM, a DVD-ROM, or a thumb drive may include the above-described notification circuit. The notification circuit may then instruct a user to perform data tests and maintenance tasks on the memory device (e.g., plug the device into a computing device and perform the tests). Alternatively, the above-described notification circuit may be enclosed in an attachment for a memory device (e.g., in a similar manner as described above with respect to attachment 302).

Additionally, device 500 and similar devices having similar notification systems (e.g., a notification system, but not including a built-in testing system) may be operated in a similar manner as described above with respect to method 400. However, device 500 and similar devices may not perform steps relating to performing a diagnostic test and/or maintenance task (e.g., performing the diagnostic test and/or maintenance task (403), outputting the results of the diagnostic test and/or maintenance task (404), and determining whether a failure or error was detected (405)). Instead, method 400 may be modified to initiate an alert via a notification circuit (e.g., notification circuit 505) to the user upon the detection of a trigger event (e.g., 404). The alert indicates that device 500 should be tested by the user.

It is important to note that the construction and arrangement of the elements of the systems and methods as shown in the embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the enclosure may be constructed from any of a wide variety of materials that provide sufficient strength or durability, in any of a wide variety of colors, textures, and combinations. Accordingly, all such modifications are intended to be included within the scope of the present inventions. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other embodiments without departing from scope of the present disclosure or from the spirit of the appended claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps, and decision steps.

What is claimed is:

1. A method of testing a data storage system in an archival state, the method comprising:
    powering a diagnostic controller of the data storage system with a power source of the storage system, wherein the data storage system is configured to be connected to a computing device;
    detecting, by the diagnostic controller, a trigger event;
    performing, by the diagnostic controller and based on detection of the trigger event, a test on the data storage system; and
    determining a result of the test;
    wherein the diagnostic controller is separate from the computing device;
    wherein detecting the trigger event includes receiving, by the diagnostic controller, a feedback signal from a detection circuit of the data storage system;
    wherein the feedback signal is indicative of a sensed physical characteristic associated with the data storage system;
    wherein the sensed physical characteristic includes at least one of a temperature, a humidity, a motion, or a magnetic field; and
    wherein the test on the data storage system is a diagnostic test including a functional test of movement of at least one of a motor or a head assembly of the data storage system.

2. The method of claim 1, wherein the detection circuit includes a sensor.

3. The method of claim 2, wherein detecting the trigger event includes determining that the sensed characteristic exceeds a threshold value.

4. The method of claim 2, wherein detecting the trigger event includes determining that a time integral of a function of the sensed characteristic exceeds a threshold value.

5. The method of claim 2, wherein the sensor includes at least one of at least one of a temperature sensor, a humidity sensor, a vibration sensor, a motion sensor, and a magnetic field sensor.

6. The method of claim 1, further comprising receiving, by the diagnostic controller, an indication of a time, a date, and/or a status of a running timer from a timer of the memory storage system.

7. The method of claim 6, wherein the trigger event is a specific time and/or a specific date.

8. The method of claim 1, further comprising initiating an alert or a message to an external computing device and/or to a user through a communication interface of the data storage system.

9. The method of claim 8, wherein the message includes a time of the test, a type of the test, a result of the test, and/or a recommended course of action.

10. The method of claim 8, wherein the communication interface includes a human-perceivable indicator.

11. The method of claim 10, wherein the human-perceivable indicator includes a light source, and wherein the message is presented through the light source such that the message is perceivable by a person.

12. The method of claim 10, wherein the human-perceivable indicator includes a speaker, and wherein the message is presented as an audible alert through the speaker.

13. The method of claim 10, wherein the human-perceivable indicator includes a display.

14. A method of indicating a need for testing of a memory storage system in an archival state, comprising:
    powering a notification circuit of the memory storage system with a power source of the memory storage system;
    detecting, by the notification circuit, a trigger event;
    providing, by the notification circuit and through a communication interface of the memory storage system, an alert external to the memory storage system that indicates a need for performing a diagnostic test of the memory storage system based on detection of the trigger event; and
    receiving, by the notification circuit, a feedback signal from a detection circuit of the memory storage system;
    wherein the feedback signal is indicative of a sensed physical characteristic associated with the memory storage system;
    wherein the sensed physical characteristic includes at least one of a temperature, a humidity, a motion, or a magnetic field; and
    wherein the trigger event is an indication that the sensed characteristic exceeds a threshold value.

15. The method of claim 14, wherein the detection circuit includes a sensor.

16. The method of claim 15, wherein detecting the trigger event includes determining that a time integral of a function of the sensed characteristic exceeds a threshold value.

17. The method of claim 15, wherein the sensor includes at least one of a temperature sensor, a humidity sensor, a vibration sensor, a motion sensor, and a magnetic field sensor.

18. The method of claim 14, further comprising receiving, by the notification circuit, an indication of a time, a date, and/or a status of a running timer from a timer of the memory storage system.

19. The method of claim 14, wherein the communication interface includes a wireless transceiver, and wherein the alert is initiated to an external computing device.

20. The method of claim 14, wherein the communication interface includes a human-perceivable indicator.

21. The method of claim 20, wherein the human-perceivable indicator includes a light source, and wherein the message is presented through the light source such that the message is perceivable by a person.

22. The method of claim 20, wherein the human-perceivable indicator includes a speaker, and wherein the message is presented as an audible alert through the speaker.

23. The method of claim 20, wherein the human-perceivable indicator includes a display.

24. A data storage and testing method comprising:
providing a storage device interface configured to connect a data storage device to an external computing device;
providing a diagnostic attachment including a diagnostic controller and an attachment interface configured to operatively connect the diagnostic attachment to the data storage device via the storage device interface;
providing operational power to the diagnostic controller using a power source; and
performing a test on the data storage device when the diagnostic attachment is operatively coupled to the data storage device using the diagnostic controller;
wherein the diagnostic attachment is separate from the external computing device; and
wherein the diagnostic attachment further includes a detection circuit configured to detect a physical characteristic associated with the data storage device and provide a feedback signal indicative of the detected characteristic to the diagnostic controller;
wherein the physical characteristic includes at least one of a temperature, a humidity, a motion, or a magnetic field; and
wherein the test on the data storage system is a diagnostic test including a functional test of movement of at least one of a motor or a head assembly of the data storage device.

25. The method of claim 24, wherein the diagnostic controller is configured to perform the test in response to an indication that the detected characteristic exceeds a threshold value.

26. The method of claim 24, wherein the diagnostic controller is configured to perform the test in response to an indication that a time integral of a function of the detected characteristic exceeds a threshold value.

27. The method of claim 24, wherein the diagnostic attachment further comprises a timer configured to provide at least one of an indication of a time, a date, and a status of a running timer.

28. The method of claim 27, wherein the diagnostic controller is configured to perform the test in response to the indication of the at least one of the present time, the present date, and the status of the running timer.

29. The method of claim 24, wherein the test includes a data test performed on the data storage device.

30. The method of claim 29, wherein the data test includes a limited check of data stored in the data storage component.

* * * * *